(12) United States Patent
Khalil et al.

(10) Patent No.: US 8,483,243 B2
(45) Date of Patent: Jul. 9, 2013

(54) NETWORK JITTER SMOOTHING WITH REDUCED DELAY

(75) Inventors: Hosam A Khalil, Redmond, WA (US);
Guo-Wei Shieh, Sammamish, WA (US);
Tian Wang, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 1190 days.

(21) Appl. No.: 11/522,268

(22) Filed: Sep. 15, 2006

(65) Prior Publication Data

US 2008/0069127 A1 Mar. 20, 2008

(51) Int. Cl.
*H04L 12/28* (2006.01)
*H04J 3/06* (2006.01)

(52) U.S. Cl.
USPC ............................ 370/517; 370/412; 370/508

(58) Field of Classification Search
None
See application file for complete search history.

(56) References Cited

U.S. PATENT DOCUMENTS

| | | | | |
|---|---|---|---|---|
| 6,434,606 | B1 * | 8/2002 | Borella et al. | 709/214 |
| 7,362,770 | B2 * | 4/2008 | Goel | 370/412 |
| 2003/0043784 | A1 * | 3/2003 | Selin | 370/352 |
| 2004/0184488 | A1 * | 9/2004 | Bauer et al. | 370/517 |
| 2006/0034338 | A1 | 2/2006 | Degenhardt et al. | |
| 2007/0177620 | A1 * | 8/2007 | Ohmuro et al. | 370/412 |
| 2008/0243495 | A1 * | 10/2008 | Anandakumar et al. | 704/214 |

FOREIGN PATENT DOCUMENTS

| | | |
|---|---|---|
| WO | 2004010670 A1 | 1/2004 |
| WO | 2005/043272 A2 | 5/2005 |

OTHER PUBLICATIONS

International Search Report issued Dec. 21, 2007 in PCT/US2007/076958 filed Aug. 28, 2007.

* cited by examiner

*Primary Examiner* — Jutai Kao
(74) *Attorney, Agent, or Firm* — Merchant & Gould

(57) ABSTRACT

A method of compensating for jitter in a packet stream is described. The method comprises placing undecoded frames extracted from packets in the packet stream into a jitter buffer while decoding frames from the jitter buffer and placing the decoded frames into a sample buffer at a rate determined using an average playout delay. The average playout delay is the running average of the playout delay calculated for each packet as each packet becomes available. The playout delay for each packet is the sum of a sample buffer delay and a jitter buffer delay. As each packet is received, the average playout delay is adjusted based on a comparison of the playout delay associated with the received packet to the current average playout delay.

14 Claims, 7 Drawing Sheets

NETWORK JITTER SMOOTHING WITH REDUCED DELAY

BACKGROUND

Communication networks used by computing devices, such as the Internet protocol (IP) network transport data in packets. Packets are bundles of data, organized in a specific way for transmission. A packet includes a header and a body. The body contains data and the header contains certain control information, including the destination address, the size of the packet, an error checking code, and so on. Data from a computing device is inserted into a packet and the packet is transmitted to another computing device that extracts and uses the data. For example, a computing device connected to a microphone may be used to record a spoken message and, using packets, transport the spoken message to a second computing device that plays back the spoken message through a speaker.

To transport a spoken message using packets, the spoken message is recorded as an analog audio signal. An analog to digital converter (ADC) is used to convert the audio signal to a digital signal. The digital signal is converted into coded binary data by a coder/decoder (codec). Encoding the binary data usually involves compressing the data. The binary data is broken into distinct frames and placed in a buffer. The packetizer extracts one or more frames from the buffer and places the frames into one or more packets. The packets are transmitted over a network to the play back computing device. A packet reader reads the packets and extracts one or more frames from the packets and places the frames into a buffer. The frames, are extracted from the buffer and the encoded binary data included in the frames is decoded and converted into a digital signal by a codec. The digital signal is converted to an analog audio signal by a digital to analog converter (DAC). The audio signal drives a speaker which reproduces the original spoken message.

Because communication networks are assemblies of physical devices, packets that are not lost take a finite amount of time to be delivered. The packet delivery time varies due to various sources of delay, such as, but not limited to, the physical distance packets travel over transmission lines, performance variations of the network routers and switches used to route the packets, and "clock drift," the timing differences between computing devices that transmit and receive the packets. Depending on the number and types of delay sources a packet encounters while being transmitted, the duration of delays vary over time. The variation in the delay of packets is called "statistical dispersion" or less formally "jitter." The more jitter in a network, the more difficult it is to maintain a constant packet delivery rate which, in turn, makes it more difficult to accurately reproduce an audio signal sent over the network.

Practically, jitter may be defined as the maximum packet delay minus the minimum packet delay over a short time period, e.g., a few milliseconds. The absolute value of the difference between the maximum packet delay and the minimum packet delay, i.e., the jitter, is not as important as having a buffer large enough to contain the number of packets received during the short time period, i.e., the short-term. Measuring jitter enables techniques for adapting an audio signal to accurately reproduce the audio output the signal represents. Preferably, signal adaptation is provided over the long-term, i.e., changes in the packet delay over a relatively long period of time, e.g., about a second. If the long term packet delay increases, the audio signal is expanded. If long term packet delay decreases, the audio signal is contracted.

There are many ways to contract and expand audio signals. For example, to contract an audio signal, small segments of the signal that contain little or no useful information may be removed; to expand an audio signal, small segments of the signal may be copied and repeated.

Compensating for jitter by signal contraction or expansion must be done carefully and not to excess. If, for example, the audio signal encodes a person's voice and the audio signal is contracted too much, the audible speech produced may seem fast. If the same audio signal is expanded too much, the audible speech produced may seem slow. Thus, the adjustments made to compensate for jitter must be done slowly enough and carefully enough that the original speech is adequately reproduced.

Traditional methods for determining when to apply jitter compensation techniques, such as signal contraction and expansion, often require that the sources of jitter be measured, quantified, and recorded as values. The values are then used to determine when to apply techniques that compensate for the effects of jitter.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method of compensating for jitter in a packet stream is disclosed. The method comprises extracting undecoded frames from the packets in the packet stream and placing the undecoded frames into a jitter buffer while decoding frames from the jitter buffer and placing the decoded frames into a sample buffer. Undecoded frames are placed into the jitter buffer and decoded frames are placed into the sample buffer at a rate determined by an average playout delay. The average playout delay is the running average of the playout delay calculated for each packet as each packet becomes available. The playout delay for each packet is the sum of a sample buffer delay and a jitter buffer delay.

As each packet is received, the average playout delay is adapted to more closely match the playout delay associated with the received packet, i.e., the current playout delay. More specifically, the current playout delay is the expected playout delay for the decoded frame or frames contained in a received packet. The current playout delay is determined as soon the decoded frame is placed into a jitter buffer. At this time a rough calculation may be made about how much longer the encoded frame will remain in the jitter buffer before the encoded frame is decoded and played, i.e., played out.

The average playout delay is compared to the current playout delay. If the current playout delay is less than the average playout delay, the value of the average playout delay is reduced. If the current playout delay is greater than the average playout delay, the value of the average playout delay is increased.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
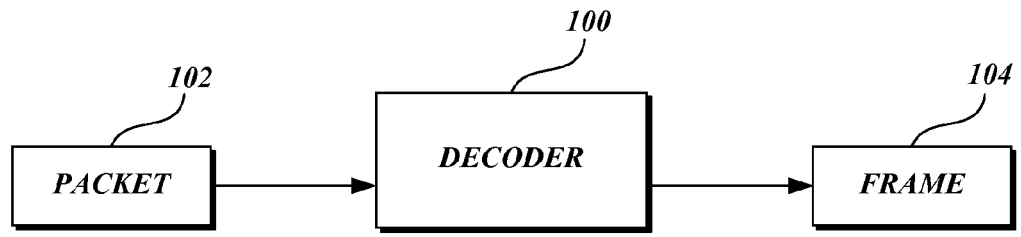
FIG. 1 is a block diagram of an exemplary synchronous data decoder.

Packets transmitted over a network, such as an IP network, that contain data, such as data describing an audio signal, are often decoded by a data decoder, i.e., decoder, as each packet is received. Usually the decoding of packets involves uncompressing compressed data contained in the packets. FIG. 1 is a block diagram illustrating an exemplary decoder 100 receiving a packet 102, decoding the data in the packet, and delivering the decoded data as a frame 104. The decoder 100 shown in FIG. 1 receives the packet 102 and delivers the frame 104 synchronously. In general, as each packet arrives at the decoder 100, the data in each packet is immediately decoded and one or more frames containing the decoded data are delivered. Frames are delivered at the same rate that the decoder 100 receives and decodes packets.

Packets transmitted over a network are often affected by jitter, i.e., the variation in packet delivery delay. Methods for counteracting the effects of jitter on synchronous decoders, such as the decoder 100 shown in FIG. 1, often require that jitter sources be measured even if the jitter sources are on remote devices. For example, the transmission delay caused by the distance a packet travels between a local device and a remote device may need to be measured, quantified, and recorded. Similarly, performance variations of the network routers and switches through which a packet travels and the clock drift of the remote and local devices may also need to be measured, quantified, and recorded in order to apply jitter compensation to synchronous decoders.

Figure 2:
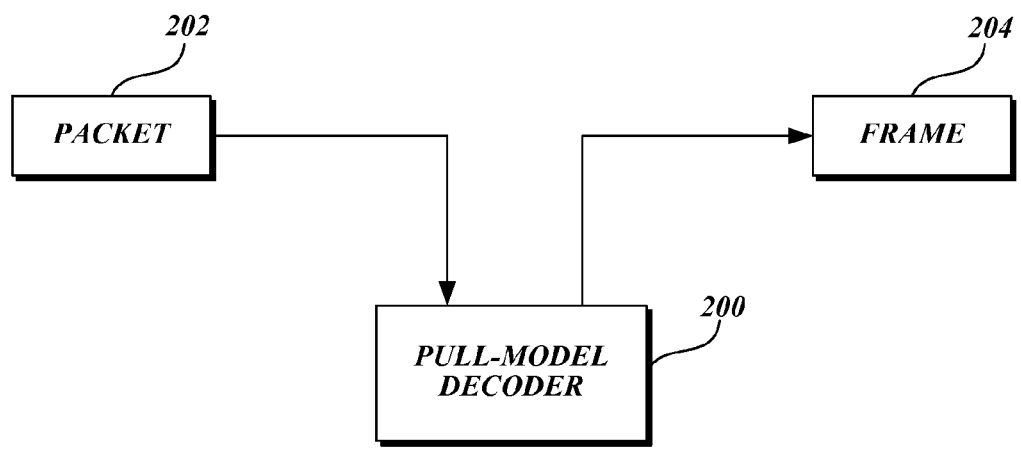
FIG. 2 is a block diagram of an exemplary asynchronous data decoder.

Asynchronous decoders, such as the pull-model decoder 200 shown in FIG. 2, are an alternative to synchronous decoders such as the synchronous decoder 100 shown in FIG. 1. A pull-model decoder is an asynchronous decoder that specifically requests data from a particular source. The pull-model decoder 200 receives a packet 202, decodes the data in the packet 202, and delivers a frame 204 containing the decoded data. Unlike a synchronous decoder, an asynchronous decoder, such as the pull-model decoder 200, receives packet 202 and delivers frame 204 asynchronously. While the pull-model decoder 200 is able to both receive packets and deliver frames at the same time, the rate at which the packets arrive and the rate at which the frames are delivered need not be the same. The rate at which packets arrive at the pull-model decoder 200 can vary without immediately changing the rate at which frames are delivered. The decoupling of the packet input rate and the frame output rate is accomplished by delivering frames as frames are requested by, for example, an audio application requiring audio frames.

Figure 3:
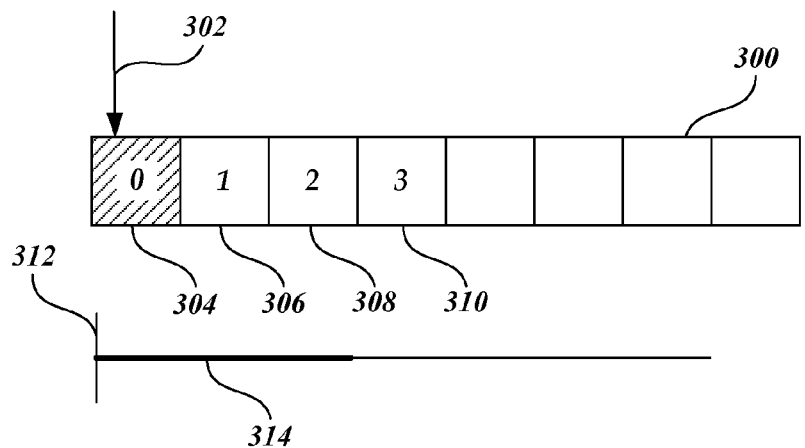
FIG. 3 is a pictorial illustration of an exemplary jitter buffer and an associated exemplary sample buffer below the jitter buffer.

A pull-model decoder, such as the pull-model decoder 200 shown in FIG. 2, uses a jitter buffer and a sample buffer to deliver frames on request. FIG. 3 illustrates an exemplary jitter buffer 300 and an associated exemplary sample buffer 312. A jitter buffer, such as exemplary jitter buffer 300, is a data buffer comprising a plurality of storage cells. Each cell in the plurality of cells is able to contain one undecoded frame. Usually, at any given time, not all of the cells contain frames. For example, cell 0 304, cell 1 306, cell 2 308 and cell 3 310 may each contain a frame and the remaining cells may not contain frames. The undecoded frames in a jitter buffer are arranged in playback order, i.e., the order in which the frame data should be played back. That is, cell 0 304 is played before cell 1 306; cell 1 306 before cell 2 308; and cell 2 308 before cell 3 310. Jitter buffer 300 includes a pointer 302 that points to the cell that is to be read and removed. The first cell of a jitter buffer, such as the cell 0 304 in the jitter buffer 300 is referred to as the "jitter head." In FIGS. 3-7, the jitter head of a jitter buffer is indicated by crosshatching. An exemplary sample buffer 312 associated with jitter buffer 300 is also illustrated in FIG. 3. The sample buffer 312 contains the decoded frame data 314 that is generated by reading, decoding, and removing frames from the jitter buffer 300.

A pull-model decoder, such as the exemplary pull-model decoder 200 shown in FIG. 2, delivers frames on request by extracting undecoded frames from packet 202 as the packet 202 is received; loading the undecoded frames into the jitter buffer 300 in playback order; and, when one or more frames are requested, delivering frames 314 from the sample buffer 312. As the frames 314 are delivered, the frames 314 are removed from the sample buffer 312. If there are no frames in the sample buffer 312, the pull-model decoder 200 reads and removes the "next" undecoded frame from the jitter buffer 300, decodes the frame, and loads the decoded frame into the sample buffer 312. The pointer 302 is thus moved to the cell that is to be read next. Preferably, the pointer 302 is kept within one or two cells of the jitter head 304. Each incoming packet is placed in a cell in the jitter buffer corresponding to the packet's sequence number. If there is a large amount of jitter, the pointer at which insert the packet moves back and forth between the first and second cells. Hence, the minimum cell placement over a short period of time should rarely come closer than about one cell from the head of the jitter buffer. If there is little or no jitter and packets arrive in order of the packets' sequence numbers, the successive packets are placed and consumed from the early part of the jitter buffer, e.g., within one frame of the jitter head. For example, a typical jitter buffer contains about one to five seconds of frame data and a typical frame contains about 20 milliseconds of data. As undecoded frames in the jitter buffer 300 are removed, the remaining undecoded frames are moved towards the jitter head 304 by moving into the next available cell.

A plurality of decoded frames in the sample buffer 312 form a contiguous sample of playable frames 314. As playable samples 314 are extracted and played from the frame buffer 312, more playable samples need to be inserted into the sample buffer 312. As new samples are required for a sample buffer 312, undecoded frames are extracted from the head of the jitter buffer 300 and the frames are decoded into samples and inserted into the sample buffer 312.

Because the delay of the arrival of packets can vary due to jitter, the rate at which frames are inserted into the jitter buffer varies compared to the rate at which frames are requested from the sample buffer 312. The method described herein compensates for this disparity by using the jitter buffer 300 as a history window. If, for example, the jitter buffer 300 is able to store enough undecoded frames to provide one second of audio data in the sample buffer, the one second jitter buffer can be viewed as one second history window. As will be better understood from the following description, the method compensates for the variation between the packet delay and the sample request rate by aligning in this example the one second jitter buffer to insure that the jitter buffer "covers" the one second of history in which the packets are being delivered. For example, a one second history window may comprise 50 cells with each cell able to contain 20 milliseconds of undecoded frame data. Preferably, the one second jitter buffer is aligned in the time dimension such that the points in time at which the data in the undecoded frames need to be played back fall within the time span covered by the jitter buffer.

Figure 4:
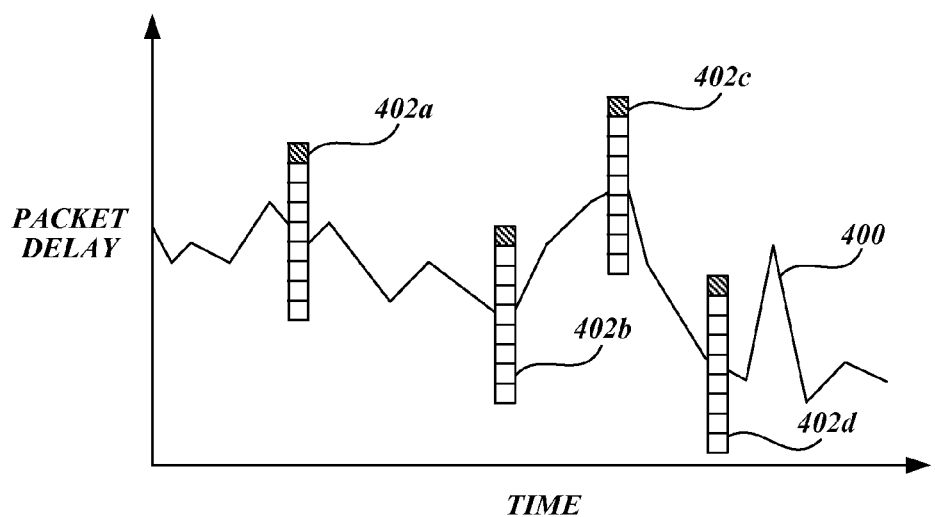
FIG. 4 is an exemplary diagram of packet delays recorded over time with a jitter buffer repositioned at various points in time.

The process of aligning a jitter buffer to cover the time span in which packets are delivered is illustrated by the exemplary diagram of packet delays recorded over time shown in FIG. 4. More specifically FIG. 4 includes a packet delay curve 400 showing packet delays recorded over time. A jitter buffer is shown in the exemplary four locations, 402a, 402b, 402c, and 402d. The jitter buffer is aligned with the packet delay curve such that location of the jitter head of the jitter buffer at the exemplary four locations, 402a, 402b, 402c, and 402d is within four cells of the packet delay curve 400. For example, the jitter buffer in position 402b is below the jitter buffer in position 402a because the packet delay curve 400 has dropped. The jitter buffer at position 402c is above the jitter buffer in position 402b because packet delay curve 400 has risen. The jitter buffer at position 402d is below the jitter buffer at position 402c because the packet delay curve has again dropped. Actual packet delays may vary more or less than the illustrated packet delay curve 400 indicates. Hence, the packet delay curve 400 should be construed as exemplary and not limiting.

Figure 5A:
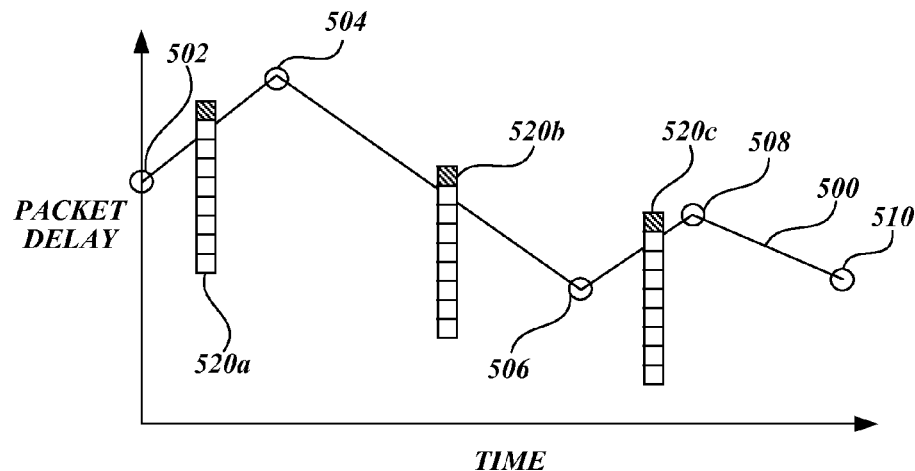
FIG. 5A is an exemplary diagram of a detailed view of packet delays recorded over time with a jitter buffer repositioned at various points in time.
Figure 5B:
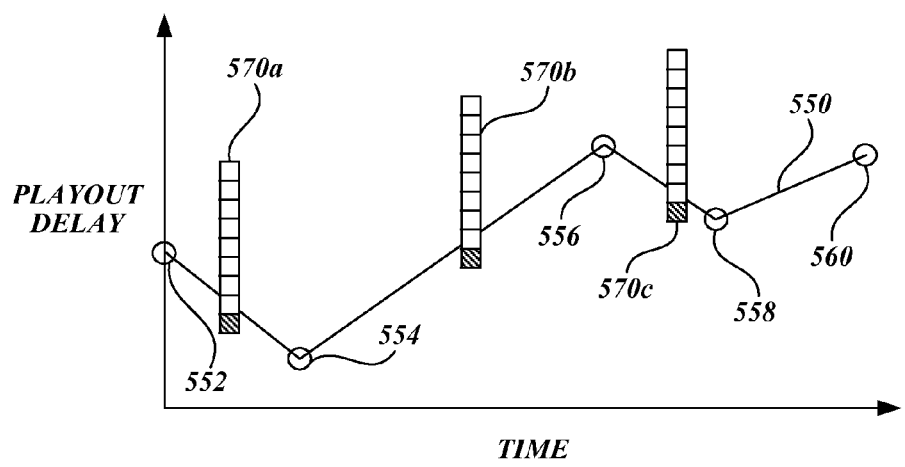
FIG. 5B is an exemplary diagram of a detailed view of playout delays recorded over time with a jitter buffer repositioned at various points in time.

In order to determine how to adjust a jitter buffer to align the jitter buffer with a packet delay curve, a playout delay is calculated. While packet delay measures the delay of a packet arriving at the decoder, playout delay estimates the time it will take for the decoded frames to be played out. In practice, a playout delay value may be nearly an inverse value of an associated packet delay. The nearly inverse relationship between packet delay and playout delay can be seen by comparing FIGS. 5A and 5B. FIG. 5A is a more detailed view of a typical section of a packet delay curve similar to the packet delay curve 400 shown in FIG. 4. FIG. 5B is a detailed view of a playout delay curve associated with the packet delay curve shown in FIG. 5A.

In FIG. 5A the packet delay curve 500 depicts packet delays over a short history window. The illustrated packet delay curve 500 defines local maxima 504, 508 and local minima 502, 506, and 510. Local maximum 504 lies between local minima 502 and 506; and local maximum 508 lies between local minima 506 and 510. A jitter buffer is shown in three positions, 520a, 520b, and 520c. Position 520a lies between local minimum 502 and local maximum 504; position 520b lies between local maximum 504 and local minimum 506; and position 520c lies between local minimum 506 and local maximum 508. The jitter buffer is positioned such that the head of the jitter buffer lies within one cell of the playout delay curve 500.

Because playout delay is nearly the inverse of packet delay, a curve representing playout delay is nearly the inverse of a curve representing packet delay. Thus, the exemplary playout delay curve 550 shown in FIG. 5B is nearly the inverse of the packet delay curve 500 shown in FIG. 5A. Because a playout delay is nearly the inverse of a packet delay, the maxima in a packet delay curve become the minima in an associated playout delay curve and the minima in a packet delay curve become the maxima in an associated playout delay curve. For example, the local minimum 502 shown in FIG. 5A becomes the local maximum 552 shown in playout delay in FIG. 5B. Similarly, local maximum 504 becomes local minimum 554; local minimum 506 becomes local maximum 556; local maximum 508 becomes local minimum 558; and local minimum 510 becomes local maximum 560.

Because a playout delay curve is nearly the inverse of a packet delay curve, the jitter buffer is also inverted such that the jitter head is at the bottom of the jitter buffer. For example, in FIG. 5A, the jitter head is at the top of the jitter buffer whereas in FIG. 5B, the jitter head is at the bottom of a jitter buffer. The jitter buffer is shown in positions 570a, 570b, and 570c. Similar to the jitter buffer aligned over the packet delay curve 500 shown in FIG. 5A, the jitter buffer is aligned over the playout delay curve 550 shown in FIG. 5B.

As noted above, the jitter buffer is shown in three positions, 570a, 570b, and 570c. These positions are aligned with positions 520a, 520b, and 520c, respectively, of FIG. 5A. At position 570a the jitter buffer overlays the section of the playout delay curve 550 between local maximum 552 and local minimum 554 within one cell of the head of the jitter buffer. At position 570b the jitter buffer overlays the section of the playout delay curve 550 between local minimum 554 and local maximum 556 within one cell of the head of the jitter buffer. At position 570c the jitter buffer overlays the section of the playout delay curve 550 between local maximum 556 and local minimum 558 within one cell of the head of the jitter buffer.

Figure 6:
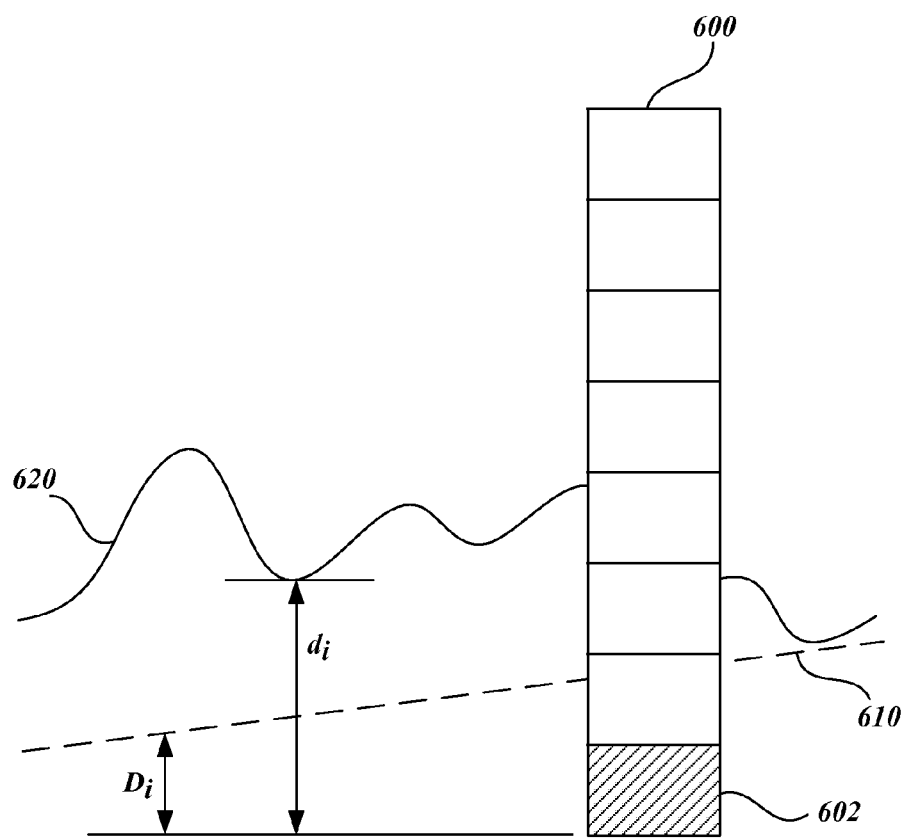
FIG. 6 is a pictorial illustration of the relationship between $d_i$, the playout delay associated with the packet, and $D_i$, the average playout delay.
Figure 7:
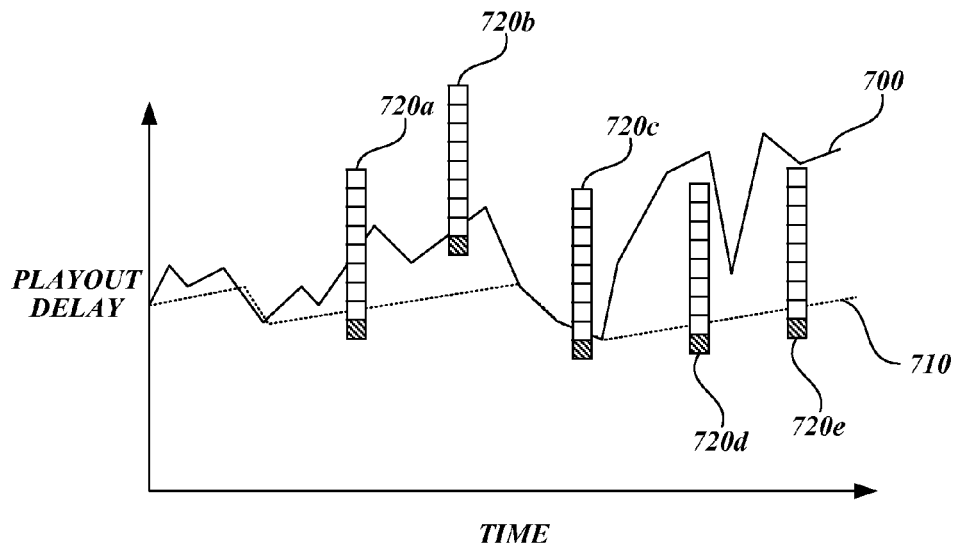
FIG. 7 is an exemplary diagram of playout delays recorded over time and a curve representing the average playout delay recorded over time.

Adjusting the position of the jitter buffer such that the jitter head overlays, or is close to overlaying, the playout delay curve within one cell of the head of the jitter buffer involves adjusting the average playout delay. FIG. 6 is a pictorial illustration of the relationships between $d_i$, the playout delay associated with a packet; $D_i$, the average playout delay; the jitter buffer 600; and the head of the jitter buffer 602. Preferably, the head 602 of the jitter buffer 600 overlays both the average playout delay curve 610 and the playout delay curve 620. The distance between the jitter head 602 and the average playout delay curve 610 is given by the distance represented by $D_i$. The distance between jitter head 602 and the playout delay curve 620, which includes a sample delay, is given by the distance represented by $d_i$.

A method for adjusting the position of the jitter buffer 600 such that the jitter head 602 overlays, or is close to overlaying, the playout delay curve 620 begins by setting a minimum delay value for jitter control, $D_{min}$, which is usually zero, and setting a maximum delay value for jitter control, $D_{max}$, which is usually zero. If a packet is available in the jitter buffer 600, the packet is decoded and the jitter buffer 600 is shifted to move the next packet into the jitter head. The decoded packet produces new samples that are appended to the last sample in the sample buffer, e.g., sample buffer 312. If a packet is not available in the jitter buffer 600, the missing packet is concealed by contracting or expanding the signal using synthesized samples and the synthesized samples used to compress or expand the signal are appended to the last sample in the sample buffer 312.

The values of $D_{max}$ and $D_{min}$, set at the beginning of the method, are used to determine whether to contract or expand the signal. If $D_i$ is greater than $D_{max}$, the signal is contracted and $D_i$ is decreased by the same corresponding time reduction. If $D_i$ is less than $D_{min}$, the signal is expanded and $D_i$ is increased by the same corresponding time increase. If $D_i$ is not greater than $D_{max}$ and $D_i$ is not less than $D_{min}$, the signal is not changed and the value of $D_i$ is changed. At this point, the requested number of samples from sample buffer 312 are returned.

Those skilled in the art will appreciate that how a signal is contracted or expanded depends on whether the signal is "voiced" or "unvoiced." A voiced signal contains useful information whereas an unvoiced signal contains silence, background noise, or sounds such as "sh" or "ss." If a signal is unvoiced, the signal may be expanded by using noise-based methods. In such expansion methods, the sample may be expanded as much as one and a half times the frame length. It is also possible to expand a sample by more or less than one and a half times the frame length. Hence, expanding a sample by as much as one and a half times the frame length should be construed as exemplary and not limiting. For example, if a frame length is 20 milliseconds, a frame may be extended by inserting noise samples until the frame's length is 30 milliseconds. If a signal is voiced, the signal may be extended by repeating pitch cycles or by generating new pitch cycles from old pitch cycles. For a voiced signal, the expanded length of the frame depends on the size of the pitch cycles. For example, if a pitch cycle spans five milliseconds, a frame's length may be extended in five millisecond increments. Thus, techniques for expanding voiced signals are signal dependent. Those skilled in the art will appreciate that to contract an unvoiced signal, samples are cut and merged using windowing or sample elimination. Usually, it is possible to contract a frame of a signal to a desired length, e.g., half of a frame length. To contract a voiced signal, pitch cycles are removed or merged. Thus, the contracted length of the frame depends on how the size of the pitch cycles and techniques for expanding voiced signals are signal dependent.

As indicated above, if a signal is contracted, the value of $D_i$ is decreased by the same corresponding time reduction; if a signal is expanded, the value of $D_i$ is increased by the same corresponding time increase. The value of $D_i$ may be adjusted according to signal contraction and expansion using signal length. If a signal has length $N_{orig}$ and the signal length becomes $N_{new}$, $D_i$ is modified as follows: $D_{i(new)} = D_{i(old)} + (N_{new} - N_{orig})/S$, where S is the sampling rate (say 16000 samples per second), and the result is in seconds. Those skilled in the art often refer to a average playout delay curve such as the average playout delay curve 610 as an "envelope." The next time a packet is received, the envelope is updated based on $D_{i(new)}$ not $D_{i(old)}$. In other words, $D_{i(new)}$ can be immediately used to overwrite $D_{i(old)}$.

Preferably, the amount by which the average playout delay $D_i$ is reduced or increased is determined according to the type of transport protocol used. For example, transmission control protocol (TCP) requires faster adaptation and hence larger adjustment amounts than user datagram protocol (UDP). For UDP, if $d_i$ is less than $D_i$, $D_{i(new)} = 0.998 * D_{i(old)} + 0.002 * d_i$; otherwise, $D_{i(new)} = d_i$. For TCP, if $d_i$ is less than $D_i$, $D_{i(new)} = 0.950 * D_{i(old)} + 0.050 * d_i$; otherwise, $D_{i(new)} = 0.9 * D_{i(old)} + 0.1 * d_i$.

An exemplary diagram illustrating the position adjustment of a jitter buffer such that the jitter head overlays the playout delay curve using the techniques described above is shown in FIG. 7. The diagram in FIG. 7 includes an exemplary playout delay curve 700, an exemplary average playout delay curve 710, i.e., envelope 710, and a jitter buffer 720 shown in five positions. The playout delay curve 700 is a solid line. The envelope 710 is a dotted line. Notice that the envelope 710 changes much more slowly over time than the playout delay curve 700. Preferably, as much as possible, the jitter head is adjusted such that the jitter head is close to the envelope 710. For example, jitter buffer 720 is shown at positions 720A, 720B, 720C, 720D, and 720E. At position 720A, 720C, 720D, and 720E, the jitter buffer is adjusted such that that jitter head is very close to the envelope 710 and the second cell of the jitter buffer overlays the envelope 710. At position 720B the jitter buffer is above the envelope 710 and the jitter head is above the envelope 710. Over time, the jitter buffer and jitter head are brought down and in alignment with the envelope 710.

Figure 8:
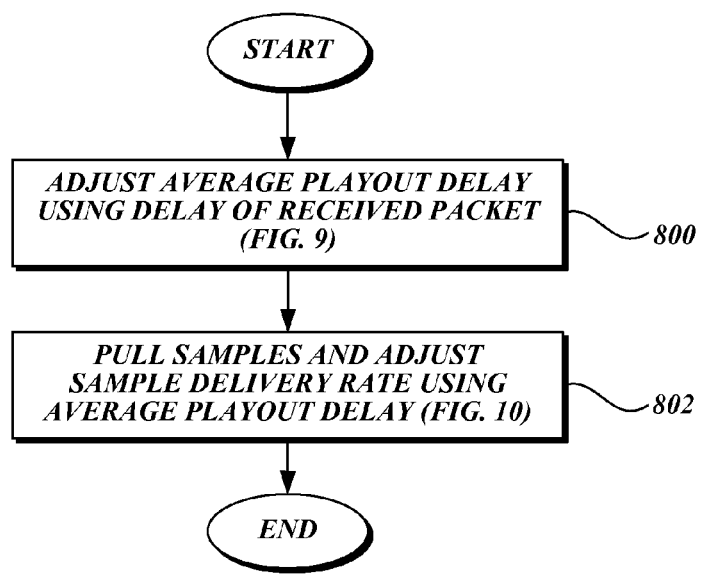
FIG. 8 is a flow diagram of an exemplary method for compensating for the effects of jitter on signals transmitted over a network.

An exemplary method for adjusting a jitter head and jitter buffer to align the jitter head with an envelope to compensate for the effects of jitter on signals transmitted over a network is illustrated by the flow diagram in FIG. 8. Note that, for most devices, when applying the exemplary method, it is preferable that samples are delivered at a constant rate. Hence, it is preferable that the samples are pulled out of the sample buffer at a constant rate. In order to accommodate changes in the amount of packet delay and still maintain a constant sample delivery rate, the samples in the sample buffer are contracted, i.e., compressed, to ensure that there are fewer samples in the sample buffer; or expanded, to ensure that there are more samples in the sample buffer. Changing the number of samples in the sample buffer indirectly controls how fast the jitter buffer is shifted. If there are more samples in the sample buffer, there is less need to shift the jitter buffer, which accommodates longer packet delays. If there are fewer samples in the sample buffer, there is more need to shift the jitter buffer, which accommodates shorter packet delays.

Figure 9:
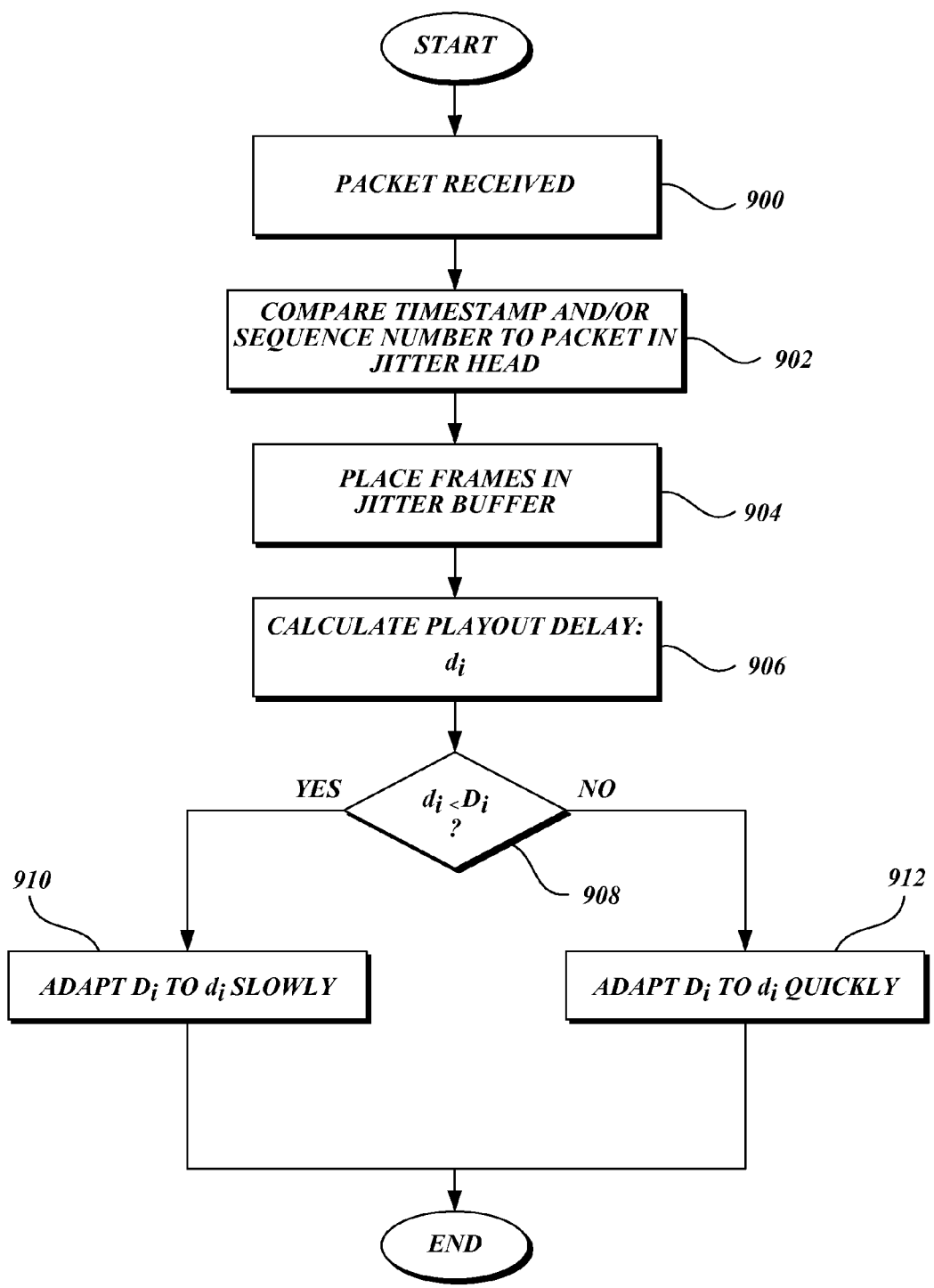
FIG. 9 is a flow diagram of an exemplary method for adjusting an average playout delay.
Figure 10:
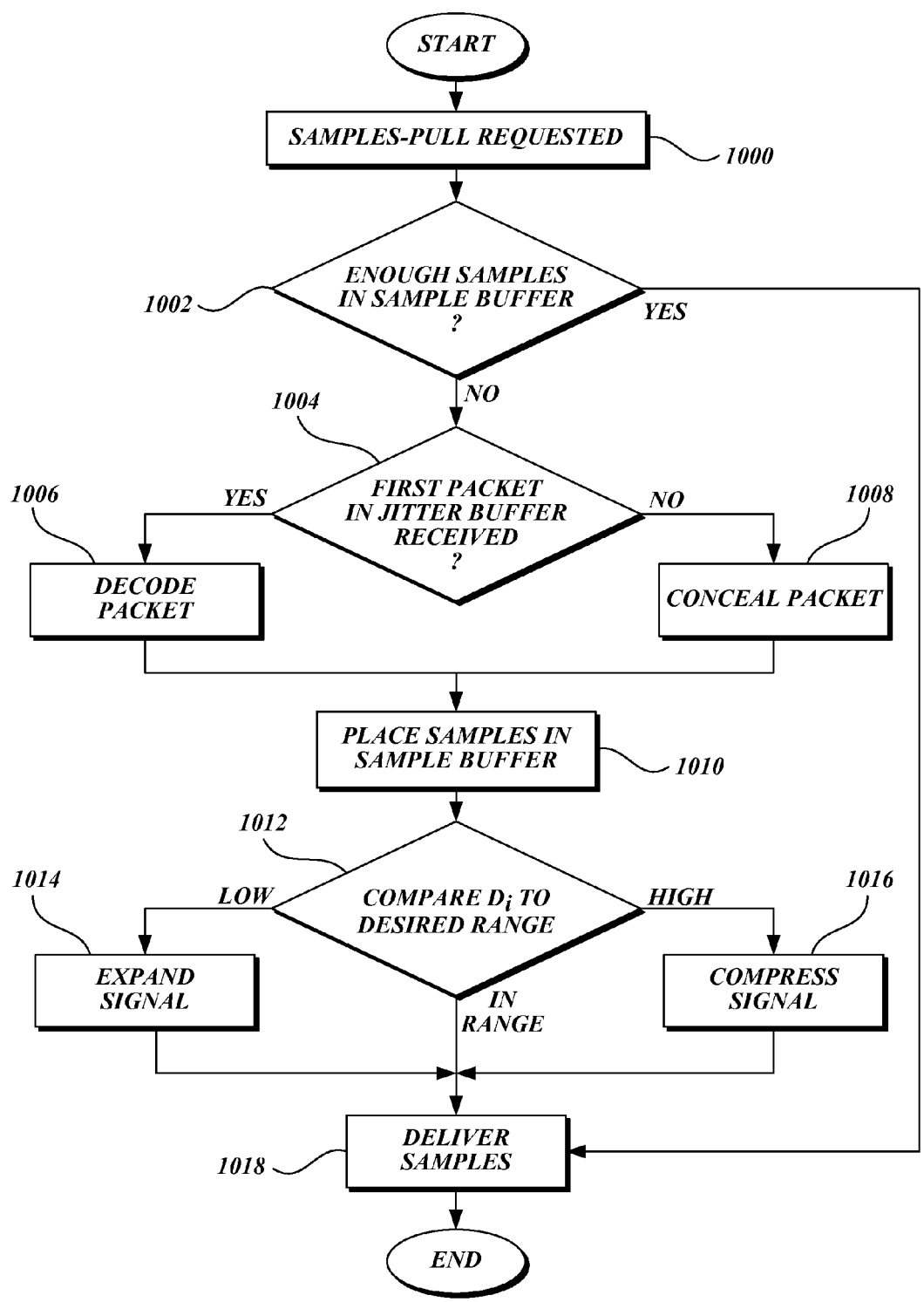
FIG. 10 is a flow diagram of an exemplary method for adjusting the delivery of frames from a sample buffer.

The exemplary method shown in FIG. 8 begins at block 800. At block 800, where a packet is received, the average playout delay is adjusted using the playout delay of the received packet as shown in FIG. 9. At block 802 samples are pulled from the sample buffer, and the sample delivery is adjusted using the average playout delay as shown in FIG. 10. Note that the action in block 800 happens asynchronously to the action in block 802. Hence, the actions in blocks 800 and 802 may be performed almost simultaneously.

FIG. 9 is a flow diagram of an exemplary method for adjusting an average playout delay, i.e., the action in block 800 of FIG. 8. The method begins at block 900 of FIG. 9 where a packet is received. At block 902 the timestamp and/or the sequence number of the received packet is compared to the packet in the jitter head. The timestamp and/or sequence number are used to determine where to place the packet in the jitter buffer. If the timestamp or sequence number indicates that the frame or frames in the packet should be placed before the frames in the jitter head packet, the jitter head frame is moved back to allow the frames in the packet to be inserted up to the jitter head. Alternatively, the timestamp or sequence number may instead indicate that the frame or frames in the packet should be placed immediately after the last occupied cell in the jitter buffer or in other cells. It is possible that there are temporary "holes" in the jitter buffer, i.e., that certain jitter buffer cells are occupied while others remain temporarily unoccupied.

In practice, the need to move the jitter head frame back to allow the frames in the packet to be inserted up to the jitter head usually occurs when the transport protocol being used is TCP and packets are delayed in large bursts. For other transport protocols, e.g., UDP, such late packets may instead be dropped allowing the jitter head frame to be shifted back one cell or not at all.

Continuing at block 904 in FIG. 9, frames, i.e., undecoded frames, are placed in the jitter buffer. At block 906, the playout delay $d_i$ is calculated. At block 908, a comparison is made between $d_i$, the playout delay, and $D_i$, the average playout delay. If $d_i$ is less than $D_i$, i.e., the playout delay is less than the average playout delay, the control flows to block 910. Otherwise, the control flows to block 912. At block 910, $D_i$ is adapted to $d_i$ slowly using the techniques described above. At block 912, $D_i$ is adapted to $d_i$ quickly using the techniques described above. After blocks 910 and 912, the method ends.

FIG. 10 is a flow diagram of an exemplary method for pulling samples and adjusting the sample delivery rate using the calculated average playout delay, i.e., the action shown in block 802 of FIG. 8. The method begins at block 1000 of FIG. 10 where a sample-pull is requested, i.e., samples from a sample buffer, such as sample buffer 312, are requested. At block 1002 a test is made to determine if enough samples are in the sample buffer. If there are enough samples in the sample buffer, the control flows to block 1018 where the samples are delivered. If there are not enough samples in the sample buffer, control flows to decision block 1004. At decision block 1004, a test is made to determine if the first packet in the jitter buffer, i.e., the packet in the jitter head, has been received. If the first packet in the jitter buffer is received, the control flows to block 1006 where the packet is decoded and the packet's decoded frames are placed in the sample buffer. If the first packet has not been received, the control flows to block 1008. At block 1008, the frames that are missing because the first packet is not available are concealed by using synthesized samples. The method continues at block 1010 where the samples, either decoded or synthesized, are placed in the sample buffer. At decision block 1012, $D_i$ is compared to the desired range for the average playout delay. If $D_i$ is within the desired range, the control flows to block 1018 where the samples are delivered. If $D_i$ is low, i.e., below the minimum of the desired range, the control flows to block 1014. If $D_i$ is high, i.e., above the maximum of the desired range, the control flows to block 1016. At block 1014, the signal is expanded using techniques described above. At block 1016, the signal is contracted using techniques described above. At block 1018, the samples are delivered and the method ends.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of compensating for jitter in a packet stream, the method comprising:
performing a first method in response to receiving each packet in the packet stream:
receiving a given packet in the packet stream;
adding a frame in the given packet to a jitter buffer;
calculating, by a computing device, a playout delay of the given packet, the playout delay of the given packet being an amount of time that the frame in the given packet is expected to remain in the jitter buffer and a sample buffer before being played out, the computing device calculating the playout delay of the given packet prior to the frame being removed from the jitter buffer; and adjusting, by the computing device, an average playout delay to more closely match the playout delay of the given packet, wherein the average playout delay is a running average of the playout delay for each packet in the packet stream; and
performing a second method, the second method comprising:
decoding a first packet in the jitter buffer after determining that there are not enough samples in the sample buffer;
placing decoded frames of the first packet into the sample buffer after decoding the first packet; and
adjusting a length of a signal represented by the samples in the sample buffer based on the adjusted average playout delay.

2. The method of claim 1, the jitter buffer having a jitter head.

3. The method of claim 2,
wherein performing the first method further comprises comparing a sequence indicator associated with the given packet to a sequence indicator associated with the packet in the jitter head;
wherein adding the frame in the given packet to the jitter buffer comprises placing the frame in the given packet into the jitter buffer based on the comparison of the sequence indicators; and
wherein adjusting the average playout delay comprises:
if the playout delay is less than the average playout delay, adjusting the average playout delay to more closely match the playout delay of the given packet by a first amount; otherwise, adjusting the average playout delay to more closely match the playout delay of the given packet by a second amount, the first amount being larger than the second amount.

4. The method of claim 3 wherein the sequence indicators are timestamps.

5. The method of claim 3 wherein the sequence indicators are sequence numbers.

6. The method of claim 3 wherein adjusting the average playout delay to more closely match the playout delay of the given packet by the second amount is based on the equation: $D_{i(new)} = 0.950 * D_{i(old)} + 0.050 * d_i$, where $D_i$ represents the distance between the jitter head and the average playout delay when the given packet is received and $d_i$ represents the playout delay of the given packet.

7. The method of claim 3 wherein adjusting the average playout delay to more closely match the playout delay of the given packet by the first amount is based on the equation: $D_{i(new)} = 0.9 * D_{i(old)} + 0.1 * d_i$, where $D_i$ represents the distance between the jitter head and the average playout delay when the given packet is received and $d_i$ represents the playout delay associated with the given packet.

8. The method of claim 3 wherein adjusting the average playout delay to more closely match the playout delay of the given packet by the second amount is based on the equation: $D_{i(new)} = 0.998 * D_{i(old)} + 0.002 * d_i$, where $D_i$ represents the distance between the jitter head and the average playout delay when the given packet is received and $d_i$ represents the playout delay of the given packet.

9. The method of claim 3 wherein adjusting the average playout delay to more closely match the playout delay of the given packet by the first amount is based on the equation: $D_{i(new)} = d_i$, where $D_{i(new)}$ represents the distance between the jitter head and the average playout delay when the given packet is received and $d_i$ represents the playout delay of the given packet.

10. The method of claim 1, wherein the method further comprises:
   determining if there are enough samples in the sample buffer to respond to a samples-pull request; and
   if there are not enough samples in the sample buffer to respond to the samples-pull request, producing additional samples for the sample buffer.

11. The method of claim 10 wherein producing additional samples for the sample buffer comprises:
   determining if the packet at a jitter head of the jitter buffer was received; and
   if the packet at the jitter head was received, decoding the packet at the jitter head;
   otherwise, concealing the packet at the jitter head.

12. The method of claim 11, wherein adjusting the length of the signal represented by the samples in the sample buffer comprises:
   comparing the adjusted average playout delay to a preselected desired range; and
   if the adjusted average playout delay is below the minimum of the desired range, expanding the signal represented by the samples in the sample buffer.

13. The method of claim 12, wherein adjusting the length of the signal represented by the samples in the sample buffer comprises: if the adjusted average playout delay is above the maximum of the desired range, contracting the signal.

14. A method of compensating for jitter in a packet stream, the method comprising:
   receiving the packet stream from a computer network via a transmission protocol;
   comparing a sequence indicator of a given packet in the packet stream with a sequence indicator of a packet in a jitter head of a jitter buffer;
   placing the given packet into the jitter buffer based on the comparison of the sequence indicator of the given packet with the sequence indicator of the packet at the jitter head of the jitter buffer;
   calculating a playout delay of the given packet when the given packet is received, the playout delay of the given packet being an amount of time that a frame in the given packet is expected to remain in the jitter buffer and a sample buffer before being played out;
   determining whether the playout delay of the given packet is less than an average playout delay, the average playout delay being a running average of playout delay of packets in the packet stream;
   in response to determining that the playout delay of the given packet is less than the average playout delay, adapting the average playout delay to the playout delay of the given packet by a first amount;
   in response to determining that the playout delay of the given packet is not less than the average playout delay, adapting the average playout delay to the playout delay of the given packet by a second amount, the first amount being larger than the second amount;
   receiving a samples-pull request;
   in response to receiving the samples-pull request, determining whether there are enough samples in the sample buffer;
   in response to determining that there are enough samples in the sample buffer, delivering at least some of the samples in the sample buffer at a rate given by the average playout delay;
   in response to determining that there are not enough samples in the sample buffer, determining whether the packet at the jitter head has been received;
   in response to determining that the packet at the jitter head has been received:
      decoding the packet at the jitter head to produce decoded samples; and
      adding the decoded samples to the sample buffer;
   in response to determining that the packet at the jitter head has not yet been received:
      generating synthesized samples; and
      adding the synthesized samples to the sample buffer;
   determining whether the average playout delay is within a desired range;
   in response to determining that the adapted average playout delay is below the desired range, expanding a signal represented by the samples in the sample buffer;
   in response to determining that the adapted average playout delay is above the desired range, compressing the signal; and
   delivering the samples in the sample buffer.

* * * * *